United States Patent [19]

Baumbach et al.

[11] Patent Number: 5,925,618
[45] Date of Patent: Jul. 20, 1999

[54] PEPTIDES USEFUL AS SOMATOSTATIN ANTAGONISTS

[75] Inventors: William Robert Baumbach, Hopewell, N.J.; Richard A. Houghten, Del Mar, Calif.

[73] Assignee: American Cyanamid Company, Madison, N.J.

[21] Appl. No.: 09/033,395

[22] Filed: Mar. 3, 1998

Related U.S. Application Data

[60] Provisional application No. 60/035,181, Mar. 6, 1997.

[51] Int. Cl.⁶ .......................... A61K 38/12; A61K 38/04; C07K 5/00; C07K 7/00
[52] U.S. Cl. .................................. 514/11; 514/9; 514/17; 530/317; 530/329
[58] Field of Search ................................... 530/329, 317; 514/17, 9, 11

[56] References Cited

U.S. PATENT DOCUMENTS

| | | | |
|---|---|---|---|
| 4,631,211 | 12/1986 | Houghten | 428/35 |
| 4,839,344 | 6/1989 | Bowers et al. | 514/16 |
| 4,880,778 | 11/1989 | Bowers et al. | 514/12 |

OTHER PUBLICATIONS

R.A. Houghten, Proceedings of the National Academy of Science, USA, 82, 5131–5135 (1985).

R.A. Houghten, et al., Nature, 354, 84–86 (1991).

C.T. Dooley, et al., Science, 266, 2019–2121 (1994).

T. Reisine, G.I. Bell, Endocrine Reviews, 16, 427–442 (1995).

L.A. Price, et al. Molecular and Cellular Biology, 15, 6188–6195 (1995).

C.M. Eppler, et al., The Journal of Biological Chemistry, 267, 15603–15612 (1992).

D.F. Veber, et al., Nature, 292, 55–58 (1981).

S.N. McCurdy, Peptide Product Formum, vol. 2, 147–152 (1989).

R.A. Bond et al., Nature, 374, 272–276 (1995).

Atherton et al., Journal of the Chemical Society, Perkin Trans. I, 2057–2064 (1985).

G.S. Tannenbaum, et al., Endocrinology, 115, 1952–1957 (1984).

*Primary Examiner*—Cecilia J. Tsang
*Assistant Examiner*—S. G. Marshall
*Attorney, Agent, or Firm*—Joseph M. Mazzarese

[57] ABSTRACT

The present invention provides peptides having pure somatostatin antagonist activity. Also provided are methods for increasing the release of growth hormone, insulin, glucagon and gastric enzymes in mammals and a method for the enhancement of immune function and growth in mammals.

30 Claims, 5 Drawing Sheets

PEPTIDES USEFUL AS SOMATOSTATIN ANTAGONISTS

This application claims priority from copending provisional application(s) Ser. No. 60/035,181 filed on Mar. 6, 1997.

BACKGROUND OF THE INVENTION

Mammalian somatostatin, a tetradecapeptide, inhibits the release of growth hormone from the pituitary gland. It further inhibits the release of insulin and glucagon from the pancreatic islet cells, inhibits secretion of gastric enzymes and inhibits immune function. Somatostatin agonists and antagonists are continually being sought to aid in the elucidation of the function of the hormone in controlling multiple physiological effects. In particular, a pure somatostatin antagonist, a compound which would successfully compete with the hormone at its receptor site, is of great interest. This compound could be used to block the inhibitory effects of somatostatin, which, in turn, would increase the release of growth hormone, insulin, glucagon and gastric enzymes and would enhance immune function. Although compounds have been discovered which demonstrate partial somatostatin antagonist activity, i.e., some agonist effect, some antagonist effect, pure somatostatin antagonists are still being sought.

Therefore, it is an object of this invention to provide a peptide having pure somatostatin antagonist activity.

It is another object of this invention to provide a method for decreasing the effect of somatostatin.

It is a further object of this invention to provide methods for increasing the release of growth hormone, insulin, glucagon and gastric enzymes in mammals and for enhancing growth and immune function in mammals.

It is a feature of this invention that the growth enhancement of meat producing animals may be effectively and readily obtained. It is an advantage of this invention that the peptide having pure somatostatin antagonist activity also demonstrates inverse agonist activity, i.e. blocks constitutive signalling by somatostatin receptors. Other features and advantages of the present invention will become apparent in the detailed description set forth below.

SUMMARY OF THE INVENTION

The present invention provides a peptide having the structure (I)

Ac—His—AA$_2$—AA$_3$—(AA$_4$)$_m$—(AA$_5$)$_n$—(AA$_6$)$_p$—NH$_2$ (II)

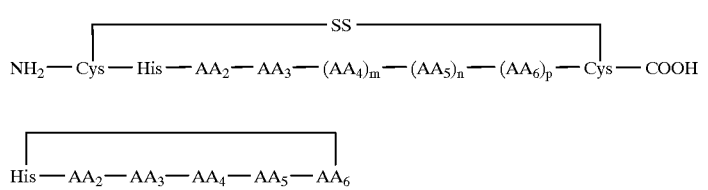

(III)

wherein:

AA$_2$ is the D or L isomer of Phe, Tyr, Trp or His;

AA$_3$ is the D isomer of a straight or branched alkyl amino acid optionally substituted with one or more OH, SH or NH$_2$ groups;

AA$_4$ is the D or L isomer of Arg, Lys, His, Asp, Asn, Gln, Tyr, Ile, Pro or Trp;

AA$_5$ is the D or L isomer of Trp, Ile, Phe, Tyr or Cys;

AA$_6$ is the D or L isomer of Phe, Tyr, Ala, Leu, Ile, Met, Gln, Trp, Asn or Thr with the proviso that only one of AA$_2$, AA$_4$, AA$_5$ or AA$_6$ may be an L isomer; and m, n and p are each independently 0 or 1 with the proviso that only one of m, n and p may be 0;

or the pharmaceutically acceptable salts thereof.

The present invention also provides a method for decreasing the effect of somatostatin. Further provided are methods for increasing the release of growth hormone, insulin, glucagon and gastric enzymes in mammals and for immune function and growth enhancement in mammals.

BRIEF DESCRIPTION OF THE DRAWINGS

The invention is described hereinbelow by way of example with reference to the accompanying drawings in which.

DETAILED DESCRIPTION OF THE INVENTION

Figure 1:
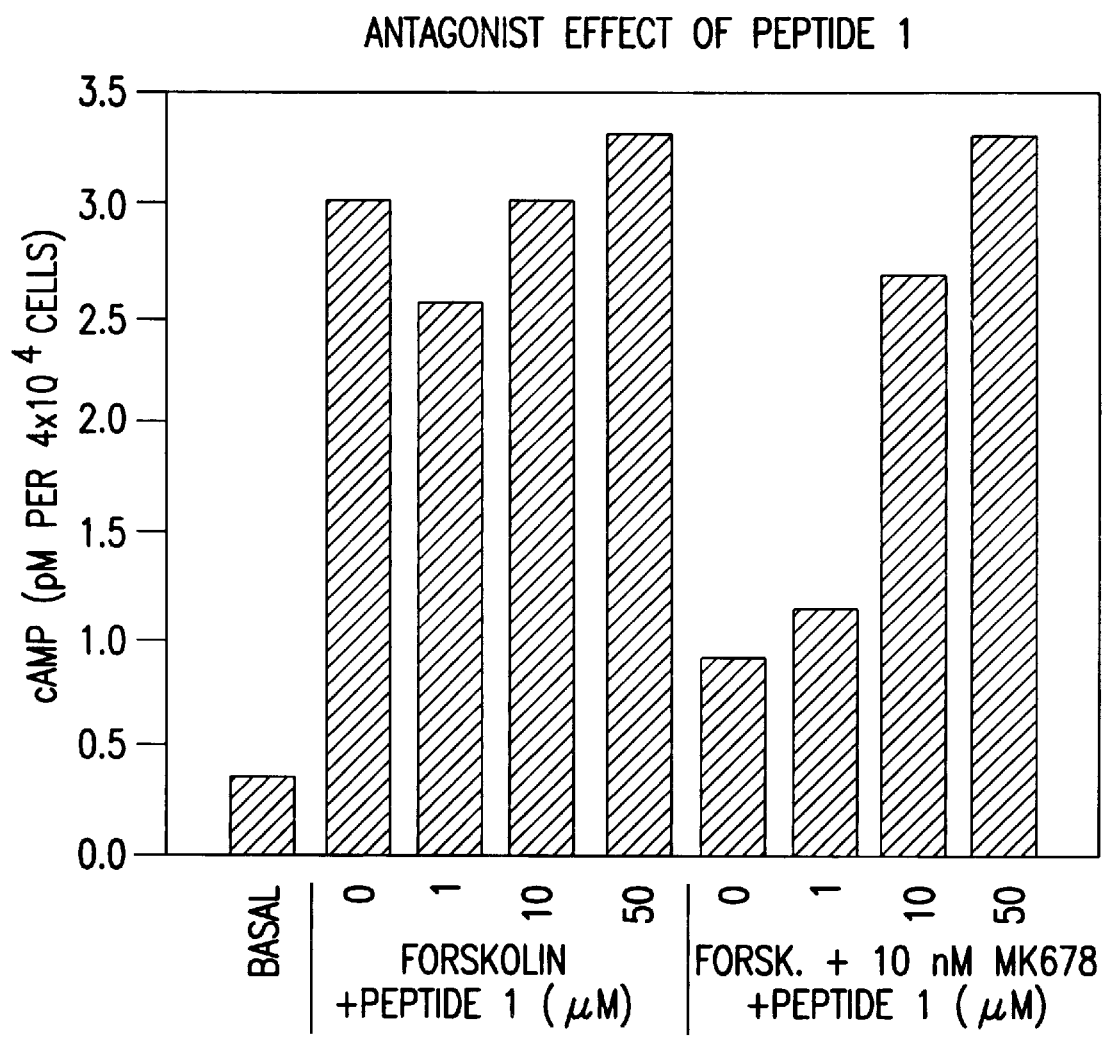
FIG. 1 illustrates the antagonist activity of peptide

Mammalian somatostatin inhibits the release of growth hormone from the pituitary gland and the release of insulin and glucagon from the pancreatic islet cells. It also has an inhibitory effect on numerous other endocrine, gastrointestinal and immune functions in mammals. A pure somatostatin antagonist could be used to effectively block the inhibitory effects of somatostatin, which would increase levels of growth hormone which in turn would increase growth in mammals, such as meat-producing animals.

Further, pure somatostatin antagonists may reverse the inhibition of immune function thus enhancing the immune function of mammals in stressful environments or serving as an adjuvant in vaccines. Therefore, pure somatostatin antagonists may be useful for the treatment of human or animal disorders where the reversal of somatostatin activity is beneficial, such as gastrointestinal or eating disorders, diabetes, brain dysfunction, and the like. In those instances where abnormally high constitutive somatostatin receptor activity leads to a disease state in mammals, treatment with an effective amount of an inverse agonist may reverse the condition, whereas a neutral antagonist would have no effect.

Surprisingly, a peptide singularly useful for decreasing the effect of somatostatin has now been found. Said peptide has the structure

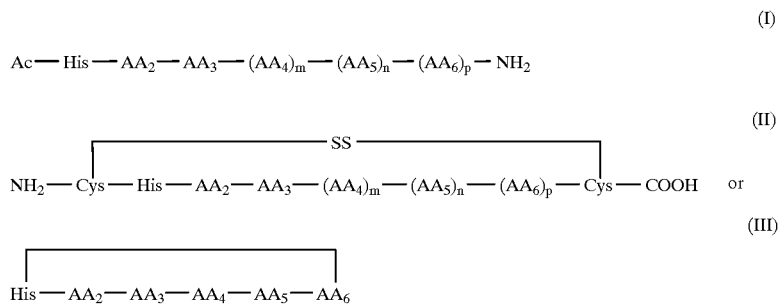

wherein:

$AA_2$ is the D or L isomer of Phe, Tyr, Trp or His;

$AA_3$ is the D isomer of a straight or branched alkyl amino acid optionally substituted with one or more OH, SH or $NH_2$ groups;

$AA_4$ is the D or L isomer of Arg, Lys, His, Asp, Asn, Gln, Tyr, Ile, Pro or Trp;

$AA_5$ is the D or L isomer of Trp, Ile, Phe, Tyr or Cys;

$AA_6$ is the D or L isomer of Phe, Tyr, Ala, Leu, Ile, Met, Gln, Trp, Asn or Thr with the proviso that only one of $AA_2$, $AA_4$, $AA_5$ or $AA_6$ may be an L isomer; and m, n and p are each independently 0 or 1 with the proviso that only one of m, n and p may be 0;

or the pharmaceutically acceptable salts thereof.

The cyclized peptides of formulas (II) and (III) are drawn in the conventional manner. The peptide of formula (II) is cyclized through a disulfide bond while the peptide of formula (III) is amide cyclized with the amino terminal of the histidine being attached to the carboxylic acid terminal of AA6.

Advantageously, the peptide of the invention demonstrates inverse agonist activity. This unique binding or signalling property allows the peptide of the invention to act as a pure somatostatin antagonist while blocking intrinsic somatostatin receptor activity, independent of endogenous somatostatin. That is, an inverse agonist has an effect on the somatostatin receptor above and beyond the blocking of the inhibitory effect of somatostatin and independent of the presence or absence of somatostatin.

The term "pharmaceutically acceptable salts" designates non-toxic acid addition salts or metal complexes which are commonly used in the human and veterinary pharmaceutical industry. Illustrative examples of acid addition salts are those organic acids such as acetic, lactic, pamoic, maleic, citric, malic, ascorbic, succinic, benzoic, palmitic, suberic, salicylic, tartaric, methanesulfonic, toluenesulfonic acid or the like; those polymeric acids such as tannic acid, carboxymethylcellulose or the like; and those inorganic acids such as hydrochloric acid, hydrobromic acid, sulfuric acid, phosphoric acid or the like. Metal complexes include zinc, iron and the like.

The notations used for the peptide amino acid residues are those abbreviations commonly used in the art and include, but are not limited to, those listed on the Table of Correspondence shown below.

Table of Correspondence

| Amino Acid | Three letter abbreviation | One letter symbol[1] |
|---|---|---|
| Alanine | Ala | A |
| Arginine | Arg | R |
| Asparagine | Asn | N |
| Aspartic Acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

[1]Lower case denotes D-isomer

Further, the abbreviation Ac as used in the specification and claims designates the acetyl radical, $CH_3CO—$.

Preferred peptides of the invention are those peptides having the structure of formula I or formula III (I)

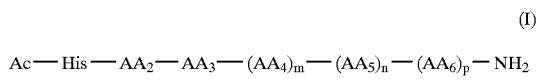

-continued

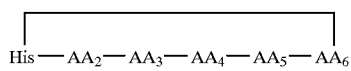
(III)

wherein $AA_2$, $AA_3$, $AA_4$, $AA_5$, $AA_6$, m, n and p are as described hereinabove.

More preferred peptides of the invention are those peptides having the structure of formula I wherein m, n and p are each 1.

Particularly preferred peptides of the invention are those peptides having the structure of formula I or III wherein the amino acids $AA_2$, $AA_4$, $AA_5$, $AA_6$ are each independently the D-isomer.

Most preferred are those peptides having the structure of formula I or III wherein $AA_2$ is the D-isomer of Phe, Trp or Tyr;

$AA_3$ is the D-isomer of Ile or Val;

$AA_4$ is the D-isomer of Arg or Lys;

$AA_5$ is the D-isomer of Trp or Tyr; and $AA_6$ is the D-isomer of Phe or Trp.

The most particularly preferred peptide of the invention is

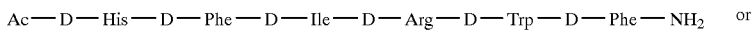

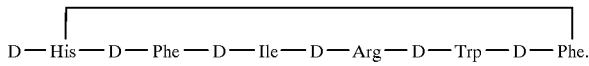

The peptide of the invention having the structure of formula I may be prepared from a synthetic combinatorial peptide library such as that described in U.S. Pat. No. 4,631,211 or by R. A. Houghton et al. in Nature, 354, 84–86, 1991, incorporated herein by reference. For example, all of the peptides in the combinatorial mixture may be acetylated at the N terminus and amidated at the C terminus to form Ac—O—O—X—X—X—X—NH$_2$ wherein O represents defined D-amino acids and X represents a random mixture of all 20 D-amino acids. The mixtures may then be biologically assayed for somatostatin activity. For mixtures that display somatostatin activity, the process of synthesis, combining, mixing, dividing equally, deprotecting, neutralizing and cleaving from the resin is repeated. This results in a peptide having the structure Ac—O—O—O—X—X—X—NH$_2$ wherein the first three D-amino acids are now defined. This peptide mixture is then assayed for somatostatin activity, followed by the above-described synthesis process and so forth until all six D-amino acid residues are defined. This procedure is similar to that described by C. T. Dooley et al. in Science 266, 2019–2022 (1994), incorporated herein by reference.

Peptides of the invention having the cyclic structures of formula II and formula III may be prepared according to conventional methods such as those described in Veber et al, Nature, 292, 55–58 (1981); McCurdy, Peptide Research, Vol. II, 147–152 (1989); and Atherton et al., *J. Chem. Soc., Perkin I*, 2057–2064 (1985), incorporated herein by reference.

Advantageously the peptide of the invention may be used to decrease the effects of mammalian somatostatin, thereby increasing the production of growth hormone, insulin, glucagon and gastric enzymes in mammals and enhancing immune function and growth in mammals. Further, the peptide of the invention may act as an inverse agonist and thereby block the deleterious effect of a constitutively active mutant somatostatin receptor.

In actual practice, the peptide of the invention may be used to block somatostatin inhibition of growth hormone release, thereby effectively facilitating growth in target species. For example, an increase in the levels of growth hormone, insulin, glucagon and gastric enzymes in a mammalian host may be obtained when the formula I peptide is administered thereto at an effective rate. Effective rates will vary according to the target host, the means of administration, the state of health of the host, the host environment, and the like. Typical effective rates include dosages of about $2 \times 10^{-6}$ mg/kg to 10.0 mg/kg of mammalian body weight per day. Said peptide may be administered orally in the drinking water or in the form of a feed additive or as a bolus, pill, tablet, oral gel, oral paste, oral drench or the like. Also contemplated is administration by parenteral intramuscular, subcutaneous, intraperitoneal or intravenous injection, or as a transdermal application, nasal spray or implant.

In order to present a more clear understanding of the invention, the following specific examples are set forth below. These examples are merely illustrative and are not to be understood as limiting the scope and underlying principles of the invention in any way. Indeed, various modifications of the invention in addition to those illustrated and described herein will become apparent to persons skilled in the art from the following examples and the foregoing description. Such modifications are also intended to fall within the scope of the appended claims.

The term, SRIF, designates somatostatin.

EXAMPLE 1

Preparation of synthetic peptide mixtures

A synthetic combinatorial peptide library is prepared using methylbenzhydrylamine (MBHA), polystyrene resin and standard t-boc chemistry as described in R. A. Houghten, et al., Nature, 354, 84–86 (1991), incorporated herein by reference. This is done in combination with simultaneous multiple peptide synthesis as described in U.S. Pat. No. 4,631,211, incorporated herein by reference.

Briefly, 20 porous polypropylene packets, each containing equal amounts of MBHA resin, are coupled to each of 20 protected D-α-t-Boc amino acids (D-enantiomers of the 20 natural L-amino acids). Coupling reactions are performed to completion, followed by combining and mixing all of the resin in each packet. This mixture is then divided equally into 20 fresh polypropylene packets followed by the removal of the D-α-t-Boc protecting groups and neutralization of the resulting amine TFA salts. This process of synthesis, combining, mixing, dividing equally, deprotecting and neutralizing is repeated four times. The resulting mixture contains equimolar amounts of every tetrameric peptide combination of 20 D-amino acids, or 160,000 different peptides, coupled to the resin. The mixture is divided again into 20 packets, for a fifth round of synthesis. This time, each of the 20 packets (in which the identity of the last amino acid is known) is separated equally into 20 packets, giving a total of 400 packets. A final (sixth) synthesis yields 400 mixtures of peptides, each of which is deprotected and cleaved from the resin using low-high hydrogen fluoride in a multiple HF cleavage apparatus (Multiple Peptide Systems, San Diego, Calif.) and extracted with water. All of the peptides are acetylated at the N-terminus, amidated at the C-terminus, and dissolved in water at a concentration of 5 mg/mL. Each of the 400 mixtures contains 160,000 peptides of the form Ac—O—O—X—X—X—X—NH$_2$, where O represents defined D-amino acids and X represents a random mixture of all 20 D-amino acids.

For mixtures that display SRIF antagonist activity in biological assays, 20 fresh samples are prepared in essentially the same procedure as the original 400 samples, except that the packets of resin are combined, mixed and divided for only three rounds of synthesis, and kept intact for three rounds of synthesis. Thus, each resulting peptide has the structure Ac—O—O—O—X—X—X—NH$_2$, whereby the first three D-amino acid positions are defined. Mixtures are again characterized for SRIF antagonist activity, followed by this synthesis process for three more rounds, whereby an additional amino acid is fully defined, until samples are isolated in which all six positions of the D-amino acid peptide hexamers are fully defined and assessed for biological activity. (See C. T. Dooley, et al., Science, 266, 2019–2022, 1994, incorporated herein by reference.

EXAMPLE 2

SRIF antagonist assay using *S. cerevisiae* (yeast) cells expressing SRIF receptors that grow in response to SRIF Agar plates containing LY364 cells that are growing in the presence of added SRIF are the basis for a sensitive SRIF antagonist assay, whereby zones of growth inhibition result from the addition of SRIF antagonists to the surface of the agar plate (see L. A. Price, et al., Molecular and Cellular Biology, 15, 6188–6195, 1995, incorporated herein by reference).

In this assay, LY364 cells are grown overnight in 2 mL of synthetic complete(SC) medium (3.4 g/L YNB without amino acids and ammonium sulfate, 10 g/L ammonium sulfate and 1.4 g/L CSM-ura-trp) with glucose (2%) and without uracil and tryptophan. These cells are washed and cultured for 4 to 8 hours in 5 mL of SC medium with lactate (3%) and without uracil and tryptophan, and finally grown overnight in 5 mL of SC medium with galactose (2%) and without uracil and tryptophan. Molten (50° C.) SC agar medium with galactose (2%) and without uracil, tryptophan and histidine is adjusted to pH 6.8 with KOH, mixed with $2 \times 10^4$ cells/mL and SRIF (S-14, 10 nM) and poured into square (20×20 cm) petri dishes. Sterile filter disks are placed on the surface of the agar, and saturated with 10 $\mu$L of water or DMSO containing 5 mg/mL test peptides. After three days, the plates display a uniform cloudy background of LY264 cells growing in response to the added SRIF. The test peptides, which diffuse radially through the agar, exhibit SRIF antagonist activity by a clear zone of growth inhibition surrounding the filter disk. This zone is quantified by measuring its diameter (mm), which varies according to the potency of the SRIF antagonist. Those peptides or mixtures of peptides displaying the largest zones of inhibition are further characterized.

Table I shows the activity of test peptides and peptide mixtures in the yeast SRIF antagonist assay. Values are compared among samples in the same experiment, as the degree of yeast growth varies somewhat from assay to assay. For the first five sample types, in which progressively less complex mixtures of peptides are found, this assay is the primary determining factor in choosing which samples form the basis of subsequent syntheses.

Plates are read after 3 days. Samples shown in Table I in bold type are chosen for further synthesis. In Table I, all amino acids are D-amino acids and dashes represent undefined amino acid residues.

TABLE I

Yeast Bioassay For SRIF Antagonist Activity

| Sample Type | $AA_1$ | $AA_2$ | $AA_3$ | $AA_4$ | $AA_5$ | $AA_6$ | Inhibition Zone (mm) |
|---|---|---|---|---|---|---|---|
| Library | His | Tyr | — | — | — | — | 12.5 |
| | His | Trp | — | — | — | — | 12 |
| | His | Phe | — | — | — | — | 13 |
| | Trp | Tyr | — | — | — | — | 12.5 |
| | Phe | His | — | — | — | — | 13.5 |
| 1st iteration | His | Phe | — | — | — | — | 5 |
| | His | Phe | Cys | — | — | — | 9 |
| | His | Phe | Val | — | — | — | 9.5 |
| | His | Phe | Leu | — | — | — | 7 |
| | His | Phe | Thr | — | — | — | 7 |
| | His | Phe | Ile | — | — | — | 10 |
| | His | Phe | Trp | — | — | — | 7 |
| 2nd iteration | His | Phe | Ile | — | — | — | 11 |
| | His | Phe | Ile | His | — | — | 11 |
| | His | Phe | Ile | Pro | — | — | 11.5 |
| | His | Phe | Ile | Arg | — | — | 12.5 |
| | His | Phe | Ile | Asn | — | — | 11 |
| | His | Phe | Ile | Trp | — | — | 11 |
| | His | Phe | Ile | Lys | — | — | 12.5 |
| 3rd iteration | His | Phe | Ile | Arg | — | — | 15 |
| | His | Phe | Ile | Arg | His | — | 12 |
| | His | Phe | Ile | Arg | Leu | — | 12 |
| | His | Phe | Ile | Arg | Arg | — | 13 |
| | His | Phe | Ile | Arg | Tyr | — | 15 |
| | His | Phe | Ile | Arg | Ile | — | 12 |
| | His | Phe | Ile | Arg | Met | — | 13 |
| | His | Phe | Ile | Arg | Trp | — | 23 |
| | His | Phe | Ile | Arg | Gly | — | 18 |
| 4th iteration | His | Phe | Ile | Arg | Trp | — | 15 |
| | His | Phe | Ile | Arg | Trp | Leu | 15 |
| | His | Phe | Ile | Arg | Trp | Thr | 14 |
| | His | Phe | Ile | Arg | Trp | Tyr | 16 |
| | His | Phe | Ile | Arg | Trp | Ile | 16 |
| | His | Phe | Ile | Arg | Trp | Ala | 15 |
| | His | Phe | Ile | Arg | Trp | Asn | 15 |
| | His | Phe | Ile | Arg | Trp | Met | 18 |
| | His | Phe | Ile | Arg | Trp | Trp | 16 |
| | His | Phe | Ile | Arg | Trp | Phe | 18 |
| | His | Phe | Ile | Arg | Trp | Gly | 13 |
| | His | Phe | Ile | Arg | Trp | Gln | 16 |

EXAMPLE 3

Evaluation of the functional activity of SRIF antagonists in vitro via cyclic AMP accumulation A primary effect of SRIF upon mammalian cells is the reduction of cyclic adenosine 3',5'-monophosphate(cAMP) levels, via inhibition of adenylyl cyclase. This is the basis of a common assay for SRIF agonists and antagonists, whereby SRIF agonists reduce artificially stimulated cAMP levels, and SRIF antagonists reverse the effect of SRIF. The rat pituitary tumor cell line $GH_4C_1$ predominantly expresses SSTR2, and responds to SRIF and to forskolin, a stimulator of adenylate cyclase (see C. M. Eppler, et al., J. Biol. Chem., 267, 15603–15612, 1992, incorporated herein by reference). A highly sensitive assay for SRIF agonists and antagonists results from additionally transfecting $GH_4C_1$ cells with the cloned rat SSTR2, (see L. A. Price, et al., Molecular and Cellular Biology, 15, 6188–6195, 1995, incorporated herein by reference). This increases the response to SRIF and provides a greater dynamic range for the measurement of SRIF antagonist activity.

Stimulation of cells. $GH_4C_1$/SSTR2 cells, grown in DMEM with 10% bovine serum, are released from a tissue culture dish by incubation for several minutes at 37° C. with PBS containing 0.5 mM EDTA. Cells are washed in induction buffer (PBS containing 100 μM IBMX (an inhibitor of cAMP breakdown) and 2 mM $CaCl_2$) at room temperature, and resuspended at $2×10^6$/mL in induction buffer. Into each well of a 96-well tray are added 50 μL of a 2× concentration of stimulants in induction buffer. These include (at final concentration) 1.25 μM forskolin, 100 nM SRIF or 10 nM of the SSTR2-selective agonist MK678 and test peptides at various concentrations. To initiate stimulation of the cells, 50 μL (100,000) cells are added to each well, mixed by shaking 10 seconds on a plate shaker and placed at 37° C. for 15 minutes. Stimulation is arrested and cells are lysed by adding 15 μL 0.33N HCl to each well and incubating the plate for 30 minutes at 37° C. Samples are neutralized by addition of 15 μL 0.25N NaOH/50 mM Hepes pH 7.4. Baseline cAMP levels are determined in samples with no added forskolin or SRIF, and each treatment is performed in triplicate.

cAMP assay. To measure accumulated cAMP in the samples, a radioimmunoassay is employed. The scintillation proximity assay (SPA, Amersham, Arlington Heights, Ill.) allows the rapid measurement of $^{125}I$ cAMP bound to a specific antibody without separating bound radioligand from free radioligand. Each of the following reagents (50 μL) are added per well in a 96-well tray: supernatants from the cell stimulation; $^{125}I$ cAMP; SPA beads conjugated to monkey anti-rabbit IgG antibodies; and rabbit anti-cAMP antibodies. For the standard curve, known amounts of cAMP (0.2–12.8 pmol) are added in place of cell supernatants. The 96-well tray is sealed, shaken at room temperature overnight and measured for bound radioligand in a MicroBeta liquid scintillation counter (Wallac, Gaithersburg, Md.). The standard curve is determined for each experiment by performing a nonlinear regression (exponential decay) analysis of cpm measured for the cAMP standards vs. their log concentrations, and test sample values are determined by using Prism software (Graphpad Software Inc., San Diego, Calif.) and are shown in Table II and FIG. 1. FIG. I illustrates the antagonist activity of Peptide 1.

The intrinsic activity of an SRIF antagonist is the percent reversal of the SSTR2, activation by SRIF or MK678, wherein 0% is defined by cAMP levels in samples treated with forskolin plus SRIF or MK678 and 100% is the cAMP level measured after treatment with forskolin alone. Therefore, increased intrinsic activity of a test compound indicates increased antagonist activity of said test compound. Table III shows the intrinsic activity of various analogs of Peptide 1.

Figure 2:
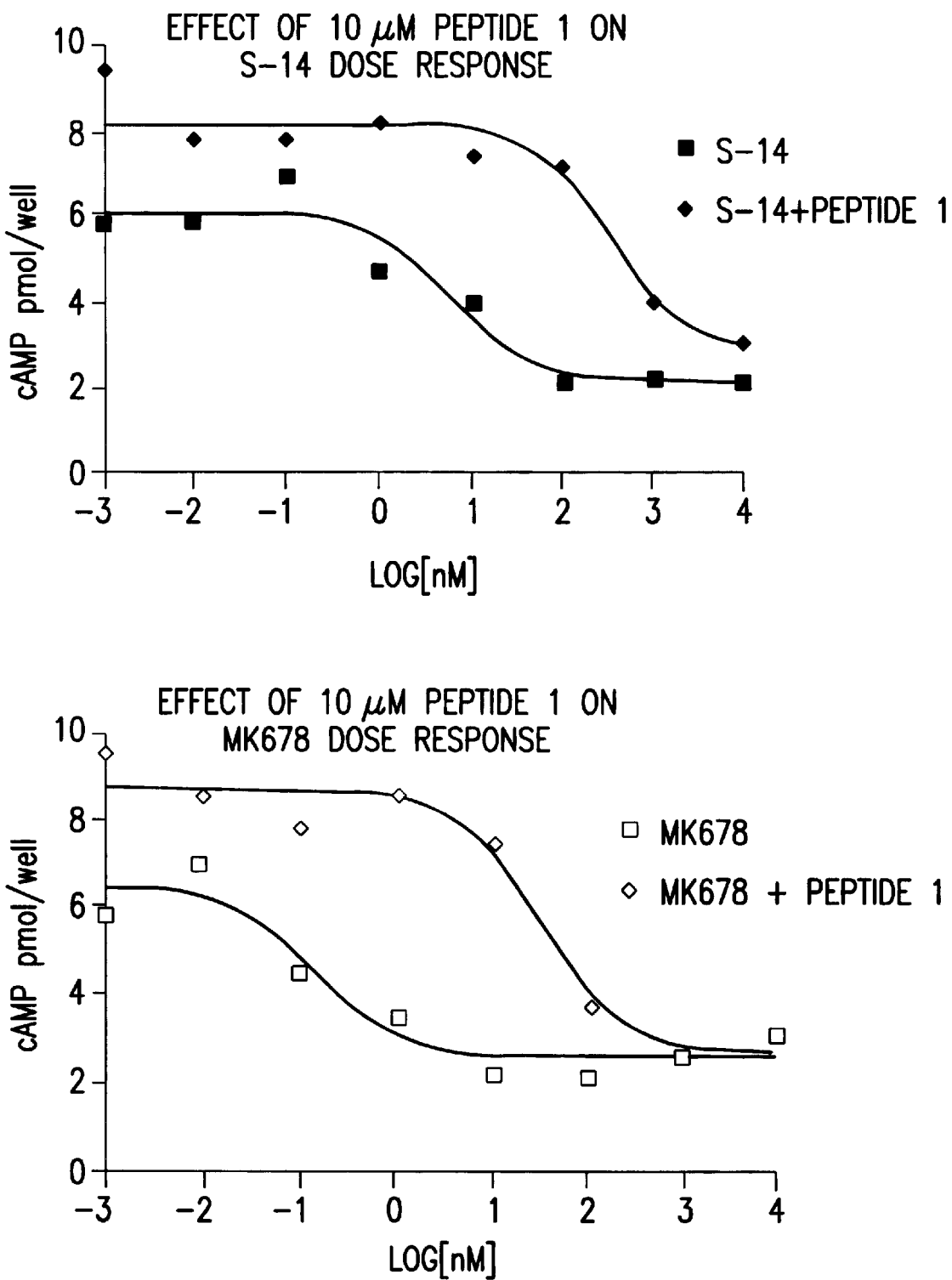
FIG. 2 illustrates the effect of peptide 1 on cAMP levels as measured in forskolin stimulated cells.

FIG. 2 (Table IV) illustrates an experiment in which cAMP levels are measured in forskolin stimulated cells with increasing doses of either S-14 or MK678, in the presence or absence of 10 mM peptide 1. The parallelism of the curves suggests that peptide 1 is directly competing with the SRIF agonists.

An inverse agonist is a compound that is not only a pure antagonist (i.e. lacking agonist activity), but also blocks the constitutive activity of an unoccupied receptor. One indication of inverse agonist activity is the ability of a SRIF antagonist to increase cAMP levels in the absence of added SRIF. This quality of Peptide 1 is illustrated in FIG. 1 (Table II) and FIG. 2 (Table IV). As can be seen, peptide 1 causes an increase in forskolin-stimulated cAMP levels even in the absence of SRIF.

TABLE II cAMP Levels In Treated $GH_4C_1$/SSTR2 Cells

| Forskolin 1.25 μM | MK 678 10 nM | Peptide 1 (μM) | cAMP[a] |
|---|---|---|---|
| − | − | — | 0.36 |
| + | − | — | 3.04 |
| + | − | 1 | 2.57 |
| + | − | 10 | 3.05 |
| + | − | 50 | 3.33 |
| + | + | — | 0.91 |
| + | + | 1 | 1.14 |
| + | + | 10 | 2.69 |
| + | + | 50 | 3.32 |

[a]pM per $4 × 10^4$ cells

TABLE III

Evaluation of Antagonist Activity of Test Compounds

| TEST | PEPTIDE | Yeast Assay(mm) | cAMP[b] Assay |
|---|---|---|---|
| | | | (2 μM) |
| 1. | h-f-i-r-w-f | 20 | 85.2 |
| 2. | a-f-i-r-w-f | none | 13.0 |
| 3. | h-a-i-r-w-f | none | 9.33 |
| 4. | h-f-a-r-w-f | 16 | 41.8 |
| 5. | h-f-i-a-w-f | 10 | 44.1 |
| 6. | h-f-i-r-a-f | 9 | 13.4 |
| 7. | f-i-r-w-f | none | −7.2 |
| 8. | h-i-r-w-f | none | 2.76 |
| 9. | h-f-r-w-f | 9 | 6.36 |
| 10. | h-f-i-w-f | 14 | 25.3 |
| 11. | h-f-i-r-f | 14 | 12.1 |
| 12. | h-f-i-r-w | 16 | 29.1 |
| 13. | H-f-i-r-w-f | 15 | 26.2 |
| 14. | h-F-i-r-w-f | 16 | 29.6 |
| 15. | h-f-I-r-w-f | 9 | 9.71 |
| 16. | h-f-i-R-w-f | 17 | 43.6 |
| 17. | h-f-i-r-W-f | 19 | 50.2 |
| 18. | h-f-i-r-w-F | 19 | 46.7 |
| 19. | k-y-i-r-w-f | 9 | 33.3 |
| 20. | h-y-i-r-w-f | 18 | 56.5 |
| 21. | h-w-i-r-w-f | 18 | 54.7 |
| 22. | w-h-i-r-w-f | none | 27.4 |
| 23. | w-y-i-r-w-f | none | 5.64 |
| 24. | f-h-i-r-w-f | none | 65.2 |
| 25. | f-r-i-r-w-f | none | 10.8 |
| 26. | h-f-i-r-g-f | 9 | 4.51 |
| 27. | h-f-i-k-w-f | 20.5 | 71.2 |
| 28. | h-f-v-r-w-f | 20 | 71.2 |
| | | | (100 μM) |
| 29. | h-w-i-r-f-f | 21.3 | |
| 30. | h-f-w-r-i-f | 12.9 | |
| 31. | h-f-r-i-w-f | 13 | |
| 32. | w-f-h-f-i-r | −6 | |
| 33. | i-r-w-f-h-f | 11.5 | |
| 34. | 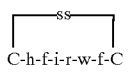 C-h-f-i-r-w-f-C | | 25.9 |
| 35. |  h-f-i-r-w-f | | 122 |

[b]Intrinsic activity

TABLE IV

Effect Of 10 μM Peptide 1 On The Dose Response Of SRIF Agonists Upon cAMP Levels In GH$_4$C$_1$/SSTR2 Cells.

|  | S-14 | S-14 + peptide 1 | MK678 | MK678 + peptide 1 |
|---|---|---|---|---|
| Maximum | 6.138 | 8.281 | 6.431 | 8.705 |
| Minimum | 2.203 | 2.883 | 2.673 | 2.775 |
| EC$_{50}$ (nM) | 6.187 | 340.1 | 0.1427 | 30.21 |

EXAMPLE 4
Evaluation of competitive binding activity of test peptides at SRIF receptors Membrane preparation. Tissue culture cell lines expressing transfected CDNA clones of SSTR2, and SSTR5 are used as a source of plasma membranes which specifically bind $^{125}$I labeled S-14 (Amersham, Arlington Heights, Ill.). Cells are removed from culture dishes by incubation at 4° C. for 5 minutes in PBS containing 1 mM EDTA, spun down (2,000 rpm, 5') and resuspended in 15 mL homogenization buffer (1 mM sodium bicarbonate pH 7.2, 1 mM EDTA, 1 mM EGTA and the following protease inhibitors: leupeptin and aprotinin at 5 μg/mL and benzamidine and bacitracin at 100 μg/mL). Cells are given 20 strokes with a Dounce homogenizer on ice and spun at 2000 rpm for 10 minutes. Membranes are isolated from the supernatant by centrifugation at 17,000 rpm for 30 minutes. The membrane pellet is washed once in 15 mL homogenization buffer and once in storage buffer (25 mM Tris pH 7.4 containing protease inhibitors). Each wash is followed by centrifugation at 17,000 rpm for 30 minutes. The membrane pellet is resuspended in storage buffer, measured for protein concentration (BioRad, Calif.) and stored at −80° C.

Binding assay. All reagents for the binding assay are prepared in binding buffer (50 mM Hepes pH 7.4, 2 mM EGTA, 5 mM MgCl2 and protease inhibitors). Membranes are thawed on ice and diluted to 1–5 mg protein/50 μL binding buffer. $^{125}$I labeled S-14 (Amersham, Arlington Heights, Ill.) is diluted to 80–100,000 cpm/50 μL in binding buffer. Competitors, either test peptides or standards, are prepared at 4× final concentrations in binding buffer, as are wheat germ agglutinin (WGA)-linked PVC beads that contain solid scintillant (SPA beads, Amersham, Arlington Heights, Ill.). The binding assay is initiated by mixing 50 μL each of membranes, radiolabelled S-14, competitors and SPA beads in each well of a 96-well tray. The assay is incubated by shaking for 10–30 minutes at room temperature and then placing at 4° C. overnight. Bound radioligand is determined by counting in a Microbeta Liquid Scintillation counter (Wallac, Gaithersburg, Md.). Binding data is plotted and IC$_{50}$ and K$_i$ values are calculated for test compounds using Prism software (Graphpad Software Inc., San Diego, Calif.) and are shown in Table V. Binding is expressed as Ki, μM.

TABLE V

Competitive Binding Activity Of Test Peptide

| Test | Peptide | SSTR2 Competitive Binding (Ki, μm) |
|---|---|---|
| 1. | h-f-i-r-w-f | 0.14 |
| 29. | h-w-i-r-f-f | 0.97 |
| 30. | h-f-w-r-i-f | 2.8 |
| 31. | h-f-r-i-w-f | 2.5 |
| 32. | w-f-h-f-i-r | 37.2 |
| 33. | l-r-w-f-h-f | 2.8 |
| 34. | C-h-f-i-r-w-f-C (with S-S bridge) 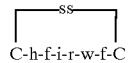 | 1.95 |
| 35. | h-f-i-r-w-f (cyclic)  | 0.14 |

EXAMPLE 5
In vivo activity of test peptides

The following experiments demonstrate the in vivo SRIF antagonist activity of test peptides in the presence of added SRIF and the in vivo SRIF antagonist activity of the test peptide alone. Such data indicate the potential use of the test peptides as therapeutics in mammals, or as growth promoters in mammals.

Figure 3:
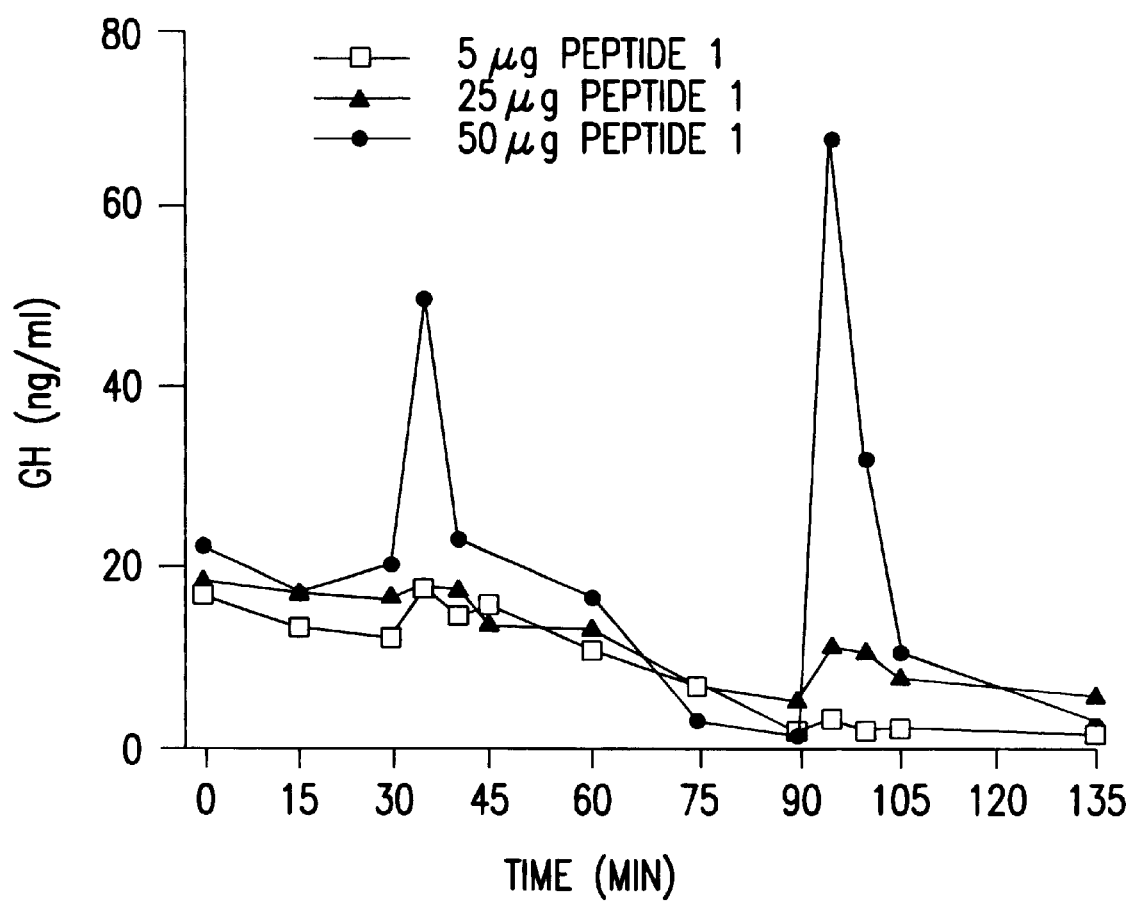
FIG. 3 illustrates the dose related effect of peptide 1 on serum growth hormone levels (GH) in vivo.

Evaluation in anaesthetized rats. Male Sprague-Dawley rats are anaesthetized with Sagatal and fitted so as to allow efficient intravenous treatment with control and test compounds as well as frequent blood sampling. Blood samples are tested for growth hormone (GH) levels by radioimmunoassay. Thirty minutes after the initiation of blood sampling, rats are given 5 μg, 25 μg or 50 μg of peptide 1. A dose related effect upon GH levels is observed, with a significant increase in serum GH levels resulting from the highest dose. Subsequently, at 60 minutes, 10 μg of the long acting SRIF agonist BIM 23014C (T. Reisine and G. I. Bell, Endocrine Reviews, 16, 427–442, 1995, incorporated herein by reference), is given, which induces the expected reduction in serum GH levels. Finally, a second dose of peptide 1 (either 5 μg, 25 μg or 50 μg) is given, inducing an even greater increase in serum GH levels from the highest dose. The data are shown in Table VI and FIG. 3.

Figure 4:
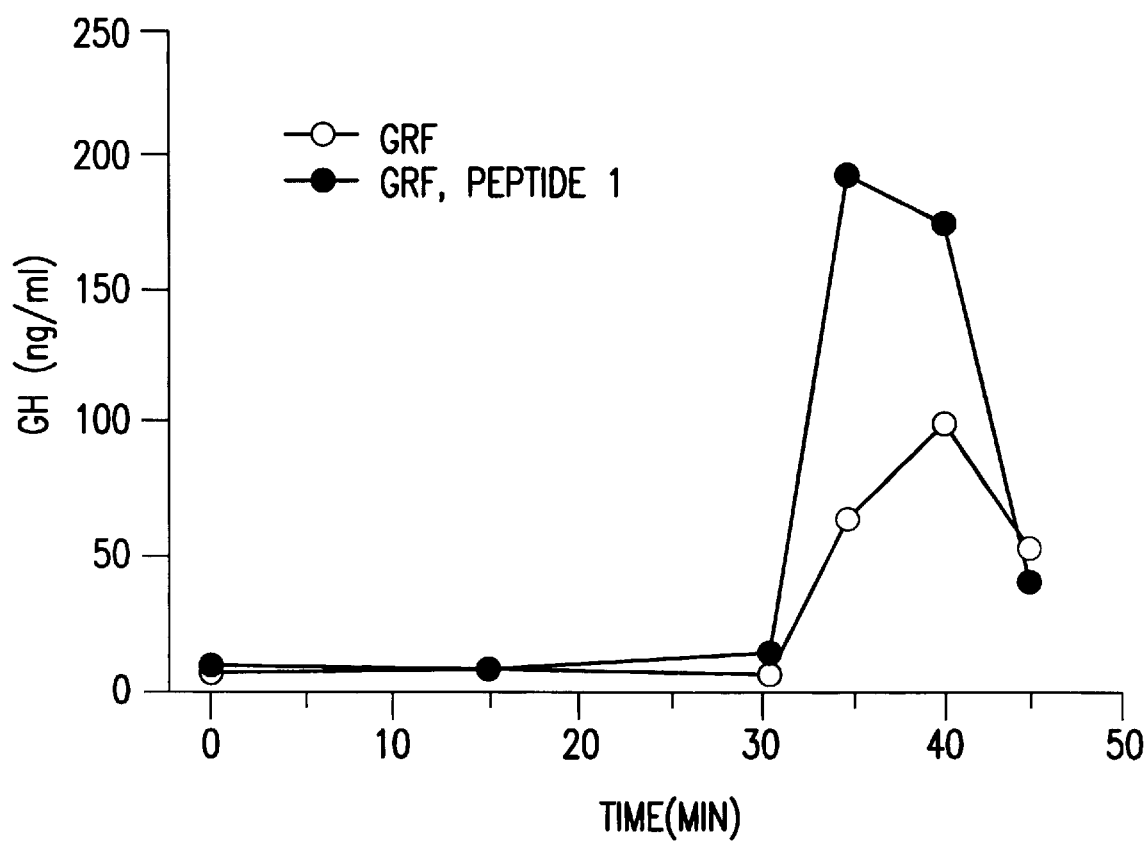
FIG. 4 illustrates the effect of growth hormone releasing factor (GRF) with and without peptide 1 in vivo.

Peptide 1 is tested in combination with growth hormone releasing factor (GRF), to investigate whether said peptide may be mimicking the action of GRF. Anaesthetized rats are given GRF (1 μg) alone and in combination with peptide 1 (50 μg). GH levels in rats treated with GRF plus peptide 1 rise faster and higher than with GRF alone, indicating that peptide 1 is not acting via the same mechanism as GRF. The data are shown in Table VII and FIG. 4.

TABLE VI

In Vivo Serum Growth Hormone Levels (SGH)

| Time (min) | Dose (μg) | SGH (ng/ml) | Dose (μg) | SGH (ng/ml) | Dose (μg) | SGH (ng/ml) |
|---|---|---|---|---|---|---|
| 0 | 0 | 17.0 | 0 | 19.2 | 0 | 22.7 |
| 15 | 0 | 13.6 | 0 | 17.3 | 0 | 17.0 |
| 30 | 5 pep$^a$ | 12.2 | 25 pep$^a$ | 16.6 | 50 pep$^a$ | 19.7 |
| 35 | 0 | 17.5 | 0 | 18.4 | 0 | 50.2 |
| 40 | 0 | 14.9 | 0 | 17.5 | 0 | 23.4 |
| 45 | 0 | 15.7 | 0 | 14.0 | 0 | 15.5 |
| 60 | 10 BIM$^b$ | 11.4 | 10 BIM$^b$ | 13.1 | 10 BIM$^b$ | 17.1 |
| 75 | 0 | 7.0 | 0 | 6.8 | 0 | 3.5 |
| 90 | 5 pep$^a$ | 2.4 | 25 pep$^a$ | 5.1 | 50 pep$^a$ | 1.9 |

TABLE VI-continued

In Vivo Serum Growth Hormone Levels (SGH)

| Time (min) | Dose (μg) | SGH (ng/ml) | Dose (μg) | SGH (ng/ml) | Dose (μg) | SGH (ng/ml) |
|---|---|---|---|---|---|---|
| 95 | 0 | 3.1 | 0 | 11.4 | 0 | 67.3 |
| 100 | 0 | 1.7 | 0 | 10.5 | 0 | 31.8 |
| 105 | 0 | 1.7 | 0 | 7.9 | 0 | 10.5 |
| 135 | 0 | 1.1 | 0 | 5.2 | 0 | 2.6 |

[a]Peptide 1
[b]BIM 23014C (SRIF agonist)

TABLE VII

In Vivo Serum Growth Hormone Levels (SGH)

| Time (min) | Dose (μg) | SGH (ng/ml) | Dose (μg) | SGH (ng/ml) |
|---|---|---|---|---|
| 0 | 0 | 11.2 | 0 | 8.9 |
| 15 | 0 | 11.3 | 0 | 11.2 |
| 30 | 1 GRF[a] | 8.4 | 1 GRF[a] + 50 Pep[b] | 16.2 |
| 35 | 0 | 67.1 | 0 | 195.8 |
| 40 | 0 | 103.5 | 0 | 176.2 |
| 45 | 0 | 53.1 | 0 | 40.5 |

[a]Growth Hormone Releasing Factor
[b]Peptide 1

Figure 5A:
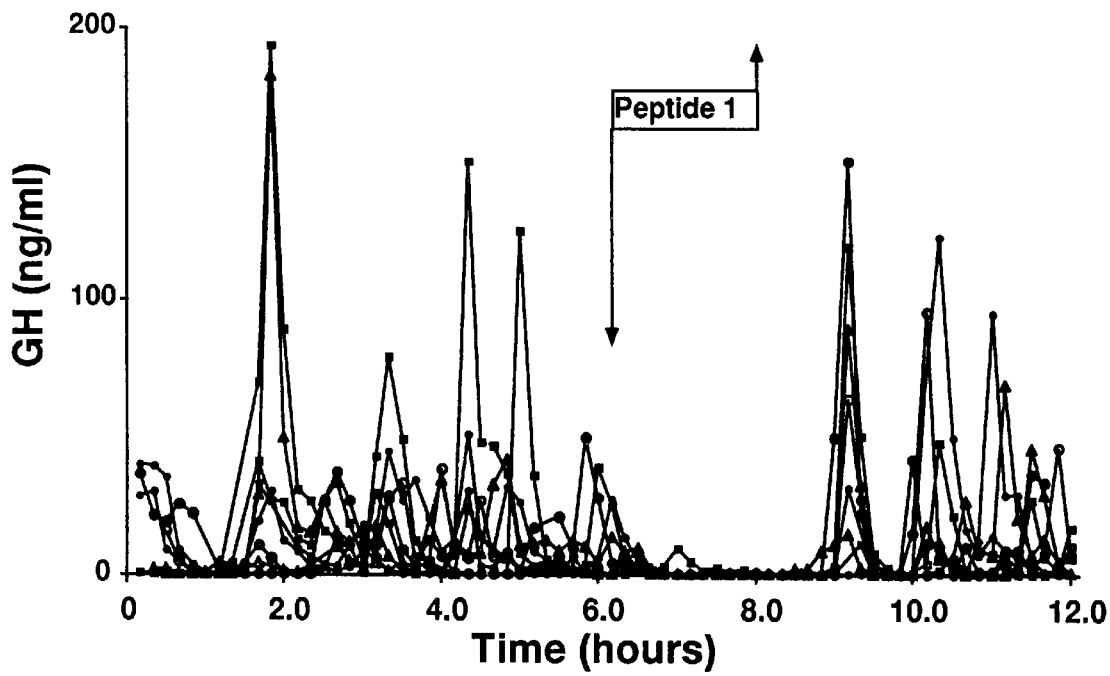
FIG. 5 illustrates the effect of peptide 1 on the spontaneous growth hormone (GH) secretory pulses in vivo.
Figure 5B:
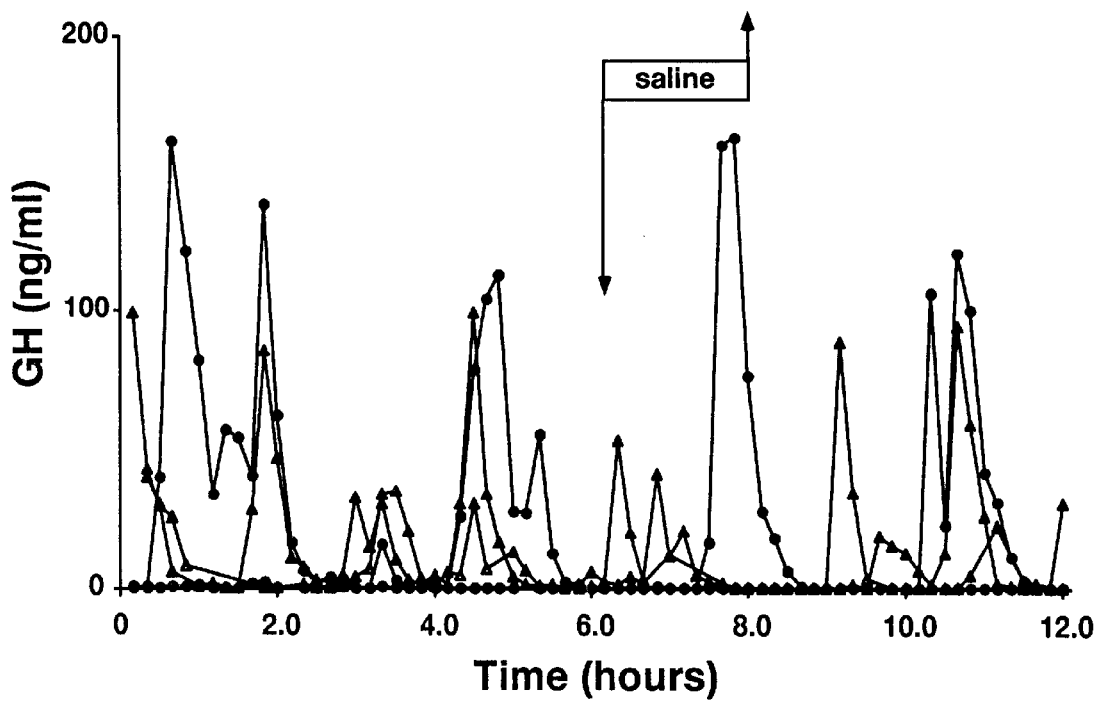

Evaluation in conscious rats. Male Sprague-Dawley rats are fitted so as to allow efficient intravenous treatment with control and test compounds as well as frequent blood sampling. Blood samples are tested for growth hormone (GH) levels by radioimmunoassay. Blood samples are taken over a 12 hour period. At a 6 hour time point, peptide 1 is infused intravenously (300 μg/hr) into conscious, freely moving male rats for two hours. Control animals receive saline infusions over the same time period. The graph in FIG. 5 illustrates the spontaneous growth hormone secretory pulses in normal male rats, and the abolition of these pulses by the infusion of peptide 1. Upon withdrawal of peptide 1, the pulses resume synchronously, and gradually desynchronize with time. It is known, SRIF is required for growth hormone pulsatility and that an SRIF antagonist abolishes said pulsatility (see Tannenbaum, G. S. and Ling, N., Endocrinology, 115, 1952–1957, 1984, incorporated herein by reference). Therefore, it can be seen in this experiment that peptide 1 demonstrates a clear effect upon the SRIF response pathway of an untreated, conscious animal, indicating that in a therapeutic setting, the peptides of the invention may be effective in counteracting the effects of SRIF.

I claim:

1. A peptide having the structure $$Ac-His-AA_2-AA_3-(AA_4)_m-(AA_5)_n-(AA_6)_p-NH_2 \quad (I)$$

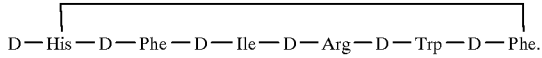
(II)

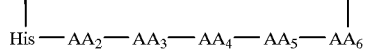
(III)

wherein:

$AA_2$ is the D or L isomer of Phe, Tyr, Trp or His;

$AA_3$ is the D isomer of a straight or branched alkyl amino acid optionally substituted with one or more OH, SH or $NH_2$ groups;

$AA_4$ is the D or L isomer of Arg, Lys, His, Asp, Asn, Gln, Tyr, Ile, Pro or Trp;

$AA_5$ is the D or L isomer of Trp, Ile, Phe, Tyr or Cys;

$AA_6$ is the D or L isomer of Phe, Tyr, Ala, Leu, Ile, Met, Gln, Trp, Asn or Thr with the proviso that only one of $AA_2$, $AA_4$, $AA_5$, or $AA_6$ may be an L isomer; and m, n and p are each independently 0 or 1 with the proviso that only one of m, n and p may be 0;

or a pharmaceutically acceptable salts thereof.

2. The peptide according to claim 1 having the structure of formula I or formula III.

3. The peptide according to claim 1 wherein $AA_2$, $AA_4$, $AA_5$ and $AA_6$ are each independently the D-isomer.

4. The peptide according to claim 1 wherein m, n and p are each 1.

5. The peptide according to claim 1 wherein $AA_2$ is the D-isomer of Phe, Trp or Tyr;

$AA_3$ is the D-isomer of Ile or Val;

$AA_4$ is the D-isomer of Arg or Lys;

$AA_5$ is the D-isomer of Trp or Tyr;

$AA_6$ is the D-isomer of Phe or Trp; and m, n and p are each 1.

6. The peptide according to claim 5 having the structure of formula I or formula III.

7. The peptide according to claim 6 Ac-D-His-D-Phe-D-Ile-D-Arg-D-Trp-D-Phe-NH$_2$.

8. The peptide according to claim 6

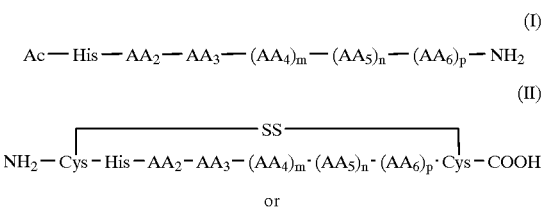

9. A method for decreasing the effect of somatostatin which comprises contacting the somatostatin receptor site with an effective amount of a peptide having the structure as defined in claim 1.

10. The method according to claim 9 having said peptide wherein $AA_2$ is the D-isomer of Phe, Trp or Tyr;

$AA_3$ is the D-isomer of Ile or Val;

$AA_4$ is the D-isomer of Arg or Lys;

$AA_5$ is the D-isomer of Trp or Tyr;

$AA_6$ is the D-isomer of Phe or Trp; and m, n and p are each 1.

11. The method according to claim 10 having the structure of formula I or III.

12. The method according to claim 11 wherein the peptide is

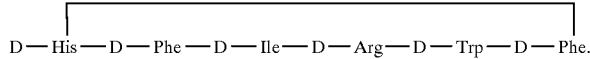

13. A method for increasing the release of growth hormone in mammals which comprises administering thereto an effective amount of a peptide having the structure as defined in claim 1.

14. The method according to claim 13 having said peptide wherein $AA_2$ is the D-isomer of Phe, Trp or Tyr;
$AA_3$ is the D-isomer of Ile or Val;
$AA_4$ is the D-isomer of Arg or Lys;
$AA_5$ is the D-isomer of Trp or Tyr;
$AA_6$ is the D-isomer of Phe or Trp; and
m, n and p are each 1.

15. The method according to claim 14 wherein the peptide is

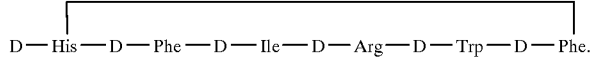

16. A method for increasing the release of insulin in mammals which comprises administering thereto an effective amount of a peptide having the structure defined in claim 1.

17. The method according to claim 15 having said peptide wherein $AA_2$ is the D-isomer of Phe, Trp or Tyr;
$AA_3$ is the D-isomer of Ile or Val;
$AA_4$ is the D-isomer of Arg or Lys;
$AA_5$ is the D-isomer of Trp or Tyr;
$AA_6$ is the D-isomer of Phe or Trp; and
m, n and p are each 1.

18. The method according to claim 17 wherein said peptide is

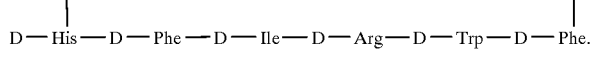

19. A method for increasing the release of glucagon in mammals which comprises administering thereto an effective amount of a peptide as defined in claim 1.

20. The method according to claim 19 having said peptide wherein $AA_2$ is the D-isomer of Phe, Trp or Tyr;
$AA_3$ is the D-isomer of Ile or Val;
$AA_4$ is the D-isomer of Arg or Lys;
$AA_5$ is the D-isomer of Trp or Tyr;
$AA_6$ is the D-isomer of Phe or Trp; and
m, n and p are each 1.

21. The method according to claim 20 wherein said peptide is

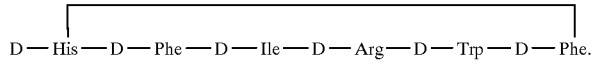

22. A method for increasing the release of gastric enzymes in mammals which comprises administering thereto an effective amount of a peptide having the structure defined in claim 1.

23. The method according to claim 22 having said peptide wherein $AA_2$ is the D-isomer of Phe, Trp or Tyr;
$AA_3$ is the D-isomer of Ile or Val;
$AA_4$ is the D-isomer of Arg or Lys;
$AA_5$ is the D-isomer of Trp or Tyr;
$AA_6$ is the D-isomer of Phe or Trp; and
m, n and p are each 1.

24. The method according to claim 23 wherein said peptide is

AC—D—His—D—Phe—D—Ile—D—Arg—D—Trp—D—Phe—NH₂   or

D—His—D—Phe—D—Ile—D—Arg—D—Trp—D—Phe.
(cyclic)

25. A method for enhancing the growth of mammals which comprises administering thereto an effective amount of a peptide having the structure defined in claim 1.

26. The method according to claim 25 having said peptide wherein $AA_2$ is the D-isomer of Phe, Trp or Tyr;

$AA_3$ is the D-isomer of Ile or Val;

$AA_4$ is the D-isomer of Arg or Lys;

$AA_5$ is the D-isomer of Trp or Tyr;

$AA_6$ is the D-isomer of Phe or Trp; and m, n and p are each 1.

27. The method according to claim 26 wherein said peptide is

AC—D—His—D—Phe—D—Ile—D—Arg—D—Trp—D—Phe—NH₂   or

D—His—D—Phe—D—Ile—D—Arg—D—Trp—D—Phe.
(cyclic)

28. A method for enhancing the immune function in mammals which comprises administering thereto an effective amount of a peptide having the structure defined in claim 1.

29. The method according to claim 28 having said peptide wherein $AA_2$ is the D-isomer of Phe, Trp or Tyr;

$AA_3$ is the D-isomer of Ile or Val;

$AA_4$ is the D-isomer of Arg or Lys;

$AA_5$ is the D-isomer of Trp or Tyr;

$AA_6$ is the D-isomer of Phe or Trp; and m, n and p are each 1.

30. The method according to claim 29 wherein said peptide is

AC—D—His—D—Phe—D—Ile—D—Arg—D—Trp—D—Phe—NH₂   or

D—His—D—Phe—D—Ile—D—Arg—D—Trp—D—Phe.
(cyclic)

* * * * *